United States Patent [19]

Robba et al.

[11] 4,079,140
[45] Mar. 14, 1978

[54] BENZOTHIENYL AMINOETHYL KETONES AND THEIR APPLICATION IN THERAPEUTICS

[75] Inventors: Max Fernand Robba; Michel Aurousseau, both of Paris, France

[73] Assignee: Innothera, Arcueil, France

[21] Appl. No.: 672,110

[22] Filed: Mar. 31, 1976

[30] Foreign Application Priority Data

Apr. 3, 1975 France .................. 75 10421

[51] Int. Cl.$^2$ .............. C07D 417/02; A61K 31/445
[52] U.S. Cl. ..................... 424/267; 260/293.57; 260/294.8 C; 260/326.34; 260/326.5 SA; 260/330.5; 424/266; 424/274; 424/275; 544/145; 424/248.51
[58] Field of Search ............. 260/293.57, 294.8 C, 260/326.34, 326.5 SA, 330.5; 424/267, 274, 264, 275

[56] References Cited

U.S. PATENT DOCUMENTS

| | | | |
|---|---|---|---|
| 3,417,087 | 12/1968 | Campaigne et al. | 260/247.1 |
| 3,903,092 | 9/1975 | Chapman et al. | 260/293.57 |

Primary Examiner—Cecilia M. S. Jaisle
Attorney, Agent, or Firm—Blanchard, Flynn, Thiel, Boutell & Tanis

[57] ABSTRACT

Compounds having the formula

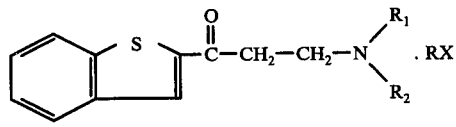

wherein $R_1$ and $R_2$ are alkyls or alkenyls having 1 to 4 atoms or

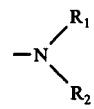

is pyrrolidino, piperidino, perhydroazepino or morpholino, and RX is a salt-forming moiety. The compounds are prepared by reacting 2-acetyl benzothiophene with

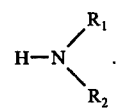

The compounds possess a blood plaque aggregation inhibiting property and also possess spasmolytic, analgesic, anti-inflammatory and coronary, cerebral and peripheral vasodilatatory properties.

6 Claims, No Drawings

BENZOTHIENYL AMINOETHYL KETONES AND THEIR APPLICATION IN THERAPEUTICS

The present invention has as its object new benzothienyl aminoethyl ketones, a method of preparation thereof and their application in therapeutics.

The compounds of the invention have the following general formula:

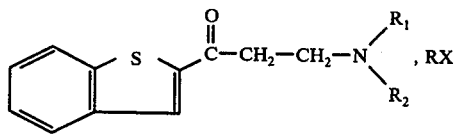

where:
- $R_1$ and $R_2$ each designate a saturated or unsaturated aliphatic hydrocarbon having 1 to 4 carbon atoms or form together with the nitrogen atom to which they are bound a heterocyclic radical chosen from the following: pyrrolidino, piperidino, perhydroazepino and morpholino; and
- RX represents an acid compound chosen from the following:
  hydrochloric acid, bromhydric acid, sulphuric acid, phosphoric acid, boric acid;
  oxalic, maleic, malic, fumaric, citric, embonic, methane sulfonic, acetylsalicylic, nicotinic, parachlorophenoxyacetic or parachlorophenoxyisobutyric acid;
  methyl bromide, methyl iodide, ethyl bromide, butyl bromide, benzyl bromide.

The method of the invention consists in condensing 2-acetyl benzothiophene of formula:

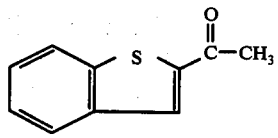

with an amine of formula:

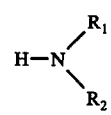

according to Mannich's reaction.

The following preparation is given as an example to illustrate the invention.

EXAMPLE 1-(benzothien-2'yl) 3-N-perhydroazepino propanone oxalate.

Compound no. 1

A mixture of 8g of 2-acetyl benzothiophene, 6g of perhydroazepine hydrochloride and 3g of trioxymethylene in 30 ml of absolute ethanol, is heated to reflux for 4 hours. After dry vacuum evaporation, 100 ml of a saturated solution of sodium carbonate is added to the residue and extracted with diethyl ether. The ether phase is washed with a saturated solution of sodium chloride and dried on anhydrous sodium sulfate. The solvent is eliminated and the residue is dissolved in the minimum of acetone. Three equivalents of oxalic acid in solution in acetone are added and the obtained mixture is heated at reflux for 30 minutes. The crystals are centrifuged after cooling and recrystallised in a mixture of methanol (1) and acetonitrile (1).

White crystals are thus obtained having a melting point of 200° C with a yield of 50%.

The compounds listed in the following table I were prepared according to the same working method.

TABLE I

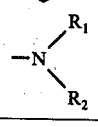

| No. of compound | $-N\begin{smallmatrix}R_1\\R_2\end{smallmatrix}$ | HX | Melting point (° C) | Crystallisation solvent | Yield (%) |
|---|---|---|---|---|---|
| 2 | $-N(CH_3)_2$ | Oxalic acid | 118 | Absolute ethanol (1) Ethyl ether (1) | 60 |
| 3 | $-N(CH_2-CH=CH_2)_2$ | Citric acid | 134 | Acetonitrile | 50 |
| 4 | piperidino | Oxalic acid | 238 | Methanol | 50 |

TABLE I-continued

Structure (I):

Benzothiophene-2-yl-C(=O)-CH$_2$-CH$_2$-N(R$_1$)(R$_2$), HX

| No. of compound | -N(R$_1$)(R$_2$) | HX | Melting point (° C) | Crystallisation solvent | Yield (%) |
|---|---|---|---|---|---|
| 5 | -N(morpholino) | Oxalic acid | 186 | Absolute ethanol | 70 |

The compounds of formula (I) were tested on laboratory animals and proved particularly active as blood-plaque aggregation inhibitors. They showed also considerable activity as spasmolytic, analgesic, anti-inflammatory and coronary, cerebral and peripheral vasodilatatory agents.

Furthermore, their toxicity was measured.

1. Acute toxicity

Acute toxicity of compounds of formula (I) was measured orally (esophageal probe) on mice deprived of food 18 hours before the beginning of the test. The products were suspended in a solution of dilute carboxymethyl cellulose. Calculation of the 50% lethal dose was carried out according to the method of Miller and Tainter (Miller L. C., Tainter M. L., proc. Soc. Exptl. Biol. Med. 1944, 57, 261-264).

The mortality rate was checked for seven days following the treatment.

Table II shows the 50% lethal doses (LD 50) in milligrammes per kilogramme of body weight.

TABLE II

| No. of compound | acute toxicity | | | | |
|---|---|---|---|---|---|
| | 1 | 2 | 3 | 4 | 5 |
| LD 50 (mg/kg/p.o.) | 1200 | 960 | 1000 | >1100 | >1100 |

2. Activity on blood-plaque aggregation

The blood-plaques used in this study are human blood-plaques introduced into the test as blood-plaque rich plasmas (B.P.R.P.). These latter are obtained as water-repellent material by slow centrifugation of human blood samples.

The study of blood-plaque aggregation is made by means of an aggregatemeter with continuous agitation and graphic recording according to the conventional method (Prost R. S., Souverain C. H., Doumenc J., Etude de l'aggrégation plaquettaire a l'aide de l'a-ggregametre de Mustard — Coagulation, 1971, 4, 2, 145-151).

The aggregation inducing agents used are diphosphoric adenosine acid (D.P.A.), 1-(3',4'-di-hydroxyphenyl) 2-methylamino ethanol (known under the name "adrenaline") and collagene. All these reactants are prepared from parent solutions diluted in Michaelis' buffer. Their concentration in the test may vary according to the affinity of the blood-plaques.

An optimal concentration is thus sought by successive tests on the same B.P.R.P.

The aggregation inhibiting activity was calculated by addition to the B.P.R.P. of the product to be tested before introduction of the aggregating agent.

The concentrations of the compounds of formula I (X) in the B.P.R.P. are $2.5 \times 10^{-5}$ g/ml for aggregation with D.P.A. and adrenaline and $2 \times 10^{-5}$ g/ml for collagene.

The reference product (R) is 2,6-bis (diethanolamino) 4,8-dipiperidinopyrimido [5,4-d] pyrimidine (known under the trademark "Dipyridamole") used in the concentration of $5 \times 10^{-4}$ g/ml for aggregation with D.P.A. and adrenaline and $2 \times 10^{-4}$ g/ml for aggregation with collagene.

The following table III shows the activity of some compounds of formula I: $a$ (X), the activity of the reference product: $a$ (R) and the different ratio values:

$$\frac{a(X)}{a(R)}$$

Furthermore, so as to have a better comparison between the activity of the compounds of the invention and that of the reference product, table III shows the ratio values:

$$\frac{C(X)}{LD\ 50\ (X)} \qquad \frac{C(R)}{LD\ 50\ (R)}$$

(we have: LD 50(R) = 2150 mg/kg/p.o.)

TABLE III

Blood-plaque aggregation inhibiting activity

| No. of compound tested | D.P.A. | | | D.P.A. or Adrenaline | Adrenaline | | | Collagene | | | |
|---|---|---|---|---|---|---|---|---|---|---|---|
| | a(X) (%) | a(R) (%) | $\frac{a(X)}{a(R)}$ | $\frac{C(X)/LD\ 50\ (X)}{C(R)/LD\ 50\ (R)}$ | a(X) (%) | a(R) (%) | $\frac{a(X)}{a(R)}$ | a(X) (%) | a(R) (%) | $\frac{a(X)}{a(R)}$ | $\frac{C(X)/LD\ 50\ (X)}{C(R)/LD\ 50\ (R)}$ |
| 1 | 54 | 72 | $7.5 \times 10^{-1}$ | $10^{-1}$ | 6 | 91 | $6 \times 10^{-2}$ | 91 | 36 | 2.5 | $1.8 \times 10^{-1}$ |
| 2 | 74 | 53 | 1.4 | $1.1 \times 10^{-1}$ | 98 | 96 | 1 | 74 | 42 | 1.75 | $2.25 \times 10^{-1}$ |
| 3 | — | — | — | $1.1 \times 10^{-1}$ | 64 | 90 | $7 \times 10^{-1}$ | 17 | 67 | $2.5 \times 10^{-1}$ | $2.15 \times 10^{-1}$ |
| 4 | 63 | 53 | 1.2 | $<1 \times 10^{-1}$ | 89 | 80 | 1.1 | 91 | 42 | 2.2 | $<1.95 \times 10^{-1}$ |

TABLE III-continued

| No. of compound tested | D.P.A. | | | D.P.A. or Adrenaline | Adrenaline | | | Collagene | | | |
|---|---|---|---|---|---|---|---|---|---|---|---|
| | a(X) (%) | a(R) (%) | $\frac{a(X)}{a(R)}$ | $\frac{\frac{C(X)}{LD\ 50\ (X)}}{\frac{C(R)}{LD\ 50\ (R)}}$ | a(X) (%) | a(R) (%) | $\frac{a(X)}{a(R)}$ | a(X) (%) | a(R) (%) | $\frac{a(X)}{a(R)}$ | $\frac{\frac{C(X)}{LD\ 50\ (X)}}{\frac{C(R)}{LD\ 50\ (R)}}$ |
| 5 | — | — | — | $<1 \times 10^{-1}$ | 44 | 96 | $4.6 \times 10^{-1}$ | 45 | 36 | 1.25 | $<1.95 \times 10^{-1}$ |

It appears that, taking into account the value of ratios:

$$\frac{\frac{C(X)}{LD\ 50\ (X)}}{\frac{C(R)}{LD\ 50\ (R)}}$$

the compounds of the invention present an inhibiting activity on blood-plaque aggregation clearly superior to that of the reference substances.

3. Spasmolytic activity

Spasmolytic activity was studied on a rat's isolated duodenum maintained in a survival medium of an aerated Tyrode solution heated to 38° C, according to the technique of Magnus (Magnus R. — Archiv. ges. Physiol., 1905, 180, 1-71).

The contracting agent was barium chloride, the reference antagonist agent being papaverine hydrochloride (R). The average activity of compounds of formula I (X) compared to that of the reference agent were expressed by calculating the ratio of 50 efficient doses (ED 50) determined graphically on logarithmic paper:

$$\frac{ED\ 50\ (R)}{ED\ 50\ (X)}$$

For example: a substance having a relative activity expressed by the figure 2 has an activity equal to twice that of papaverine hydrochloride.

The results obtained shown in table IV show that the compounds of the invention have an interesting spasmolytic activity.

TABLE IV

| No. of compound tested | Spasmolytic activity | | |
|---|---|---|---|
| | ED 50 (X) (g/ml) | ED 50 (R) (g/ml) | $\frac{ED\ 50\ (R)}{ED\ 50\ (X)}$ |
| 2 | $1.6 \times 10^{-6}$ | $4.25 \times 10^{-6}$ | 2.64 |
| 4 | $3.10 \times 10^{-6}$ | $5.25 \times 10^{-6}$ | 1.69 |

4. Analgesic and anti-inflammatory activity

The intraperitoneal injection of phenylparaquinone (P.P.Q.) to a mouse causes the appearance of a painful syndrome appearing within 5 minutes of the injection and disappearing after about 30 minutes (Siegmund E. A., Cadmus A., Lu G., J. Pharmacol. Exp. Therap. 1957, 119, 453).

This painful syndrome manifests itself in the animal by a series of characteristic crises more or less close together and fleeting, during which can be noted a twisting or stretching of the body, a hollowing of the sides and a stretching of the hind legs.

It is then possible to note the number of crises in a given interval of time.

The preventive administration of analgesic or anti-inflammatory substances prevents the appearance of the crises and reduces the frequence thereof.

The reference substance used in the tests (R) is the ester of N-(7-chloro-4-quinolyl) anthrilic acid and 2,3-dihydroxy n. propanol (known under the trademark "Glafenine").

It is administered orally as a dose of 25 mg/kg.

The compounds of formula I (X) were administered digestively as a dose of 50 mg/kg.

The interval of time (t) chosen for calculating the analgesic activity was between 10 and 15 minutes after injection of P.P.Q. which is the period of maximum frequency of the crises. This activity was expressed in the following manner;

n: the number of crises observed in controle mice;
n': the number of crises observed in mice previously treated with the reference substance (R);
n": the number of crises observed in mice having received substance (X)

The percentage activity of R is equal to:

$$\frac{(n - n') \times 100}{n} = a\ (R)$$

The percentage activity of X is equal to:

$$\frac{(n - n'') \times 100}{n} = a\ (X)$$

The activity of X in relation to R is estimated by the ratio:

$$\frac{a\ (X)}{a\ (R)}$$

For example, a compound X for which:

$$\frac{a\ (X)}{a\ (R)}$$

is calculated as 0.5 possesses an activity equal to half that of the reference product.

The following table V shows the results observed.

TABLE V

| No. of compound tested | Analgesic and anti-inflammatory activity (P.P.Q.) | | | |
|---|---|---|---|---|
| | a (X) | a (R) | $\frac{a\ (X)}{a\ (R)}$ | Adm. dose (X) LD 50 (X) |
| 2 | 36 | 71 | 0.51 | $5.2 \times 10^{-2}$ |
| 3 | 58 | 77 | 0.75 | $5 \times 10^{-2}$ |
| 4 | 25 | 75 | 0.33 | $<4.5 \times 10^{-2}$ |
| 5 | 54 | 71 | 0.76 | $<4.5 \times 10^{-2}$ |

It is clear that the reference product is more active than the compounds of the invention. Nevertheless, these latter present an interesting analgesic and anti-inflammatory activity since their activity represents a substantial fraction of that of the reference product which is an excellent analgesic.

5. Vasodilatatory activity

The dilatatory activity as regards the smooth musculature of the vessels was demonstrated on the isolated heart of a guinea-pig perfused with a Locke solution maintained at 37° C, after having provided the aorta with a cannula.

The coronary flow is recorded by means of an electronic device comprising a Fleish totaliser, before and after addition of substance X to be studied (concentration: $1 \times 10^{-5}$ g/ml), the reference product being 2,6-bis (diethanolamino) 4,8 dipiperidino pyrimido [5, 4-d] pyrimidine (known under the trademark "Dipyridamole") used in a concentration of $1 \times 10^{-5}$ g/ml.

The percentage of flow increase (P) is calculated at the climax of the activity of X or R.

The following table shows the results observed.

TABLE VI

| No. of compound | vasodilatatory activity | | |
|---|---|---|---|
| | P (X) | P (R) | P (X)/P (R) |
| 1 | 66 | 76 | 0.87 |
| 2 | 64 | 162 | 0.4 |

These pharmacological results show the interest of compounds of formula I in the treatment of coronary and cardiac inadequacies, pains of inflammatory and other origins and spasms.

The new derivatives can be presented for oral, rectal or parenteral administration in man and animals, particularly in association with the excipients appropriate to these ways of administration.

Thus for example, they can be presented in the form of tablets, pills, gelules, suppositaries or injectable solutions.

The daily dose can, according to the case, be between 50 and 600 mg.

What we claim is:

1. A compound having the formula (I):

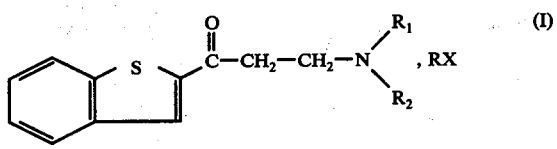

where:
R$_1$ and R$_2$ each is alkyl or alkenyl having up to 4 carbon atoms or form together with the nitrogen atom to which they are bound pyrrolidino, piperidino or perhydroazepine; and RX is selected from the group consisting of
hydrochloric acid, bromhydric acid, sulphuric acid, phosphoric acid, boric acid,
oxalic acid, maleic acid, malic acid, fumaric acid, citric acid, methane sulfonic acid, acetylsalicylic acid, nicotinic acid, parachlorophenoxyacetic acid, parachlorophenoxyisobutyric acid,
methyl bromide, methyl iodide, ethyl bromide, butyl bromide and benzyl bromide.

2. A compound as claimed in claim 1, 1-(benzothien-2'-yl)3-N-perhydroazepino propanone oxalate.

3. A compound as claimed in claim 1, 1-(benzothien-2'-yl)-3-dimethylamino propanone oxalate.

4. A compound as claimed in claim 1, 1-(benzothien-2'-yl)-3-diallylamino propanone citrate.

5. A compound as claimed in claim 1, 1-(benzothien-2'-yl)-3-N-piperidino propanone oxalate.

6. A therapeutic composition useful as a blood plaque aggregation inhibitor, a spasmolytic agent, an analgesic agent, an anti-inflammatory agent, a coronary vasodilatatory agent, a cerebral vasodilatatory agent or a peripheral vasodilatatory agent, comprising an effective amount of a compound as claimed in claim 1 in combination with a pharmacologically acceptable carrier.

* * * * *